United States Patent [19]

Schmid-Schönbein et al.

[11] Patent Number: 4,474,538
[45] Date of Patent: Oct. 2, 1984

[54] METHOD AND APPARATUS FOR CIRCULATING OR PUMPING ORGANO-BIOLOGICAL LIQUIDS, IN PARTICULAR BLOOD

[76] Inventors: Holger Schmid-Schönbein, Am Tittardshang 1A; Khosrow Mottaghy, Walhornerstr. 1A, both of 5100 Aachen; Heinz Myrenne, Steffensgasse 9, 5106 Roetgen/Kreis Aachen, all of Fed. Rep. of Germany

[21] Appl. No.: 542,910

[22] Filed: Oct. 18, 1983

Related U.S. Application Data

[63] Continuation of Ser. No. 156,463, Jun. 4, 1980, abandoned.

[30] Foreign Application Priority Data

Jun. 6, 1979 [DE] Fed. Rep. of Germany ....... 2922957

[51] Int. Cl.³ .............................................. A61M 1/03
[52] U.S. Cl. ................................ 417/53; 128/DIG. 3; 128/DIG. 12; 417/320; 417/572; 604/4; 604/141
[58] Field of Search .......................... 417/53, 320, 572; 128/DIG. 3, DIG. 12; 604/4, 140, 141, 147, 153

[56] References Cited

U.S. PATENT DOCUMENTS

| 2,291,912 | 8/1942 | Meyers ................................ 417/394 |
| 3,017,885 | 1/1962 | Robicsek ....................... 128/DIG. 3 |
| 3,684,405 | 8/1972 | Wright et al. ...................... 417/394 |
| 3,811,800 | 5/1974 | Shill ................................ 417/394 X |
| 3,892,236 | 1/1975 | Djerassi .......................... 128/214 R |
| 3,955,557 | 5/1976 | Takagi ............................ 417/394 X |
| 4,250,872 | 2/1981 | Tamari ............................ 417/394 X |

OTHER PUBLICATIONS

Boretos, J. W. et al., Segmented Polyurethane: A Polyether Polymer, J. Biomed. Mater. Res., vol. 2, pp. 121–130 (1968), 128-DIG. 3.

Mustard, W. T. et al., Further Observations on Experimental Extracorporeal Circulation, Surgery, vol. 32, No. 5, pp. 803–810, Nov. 1952, 128-DIG. 3.

Primary Examiner—Leonard E. Smith
Attorney, Agent, or Firm—Cushman, Darby & Cushman

[57] ABSTRACT

The present invention relates to a method of circulating organo-biological liquids, preferably blood, wherein a liquid contained in a reservoir is released to a pressure (head) level below its original fluid pressure (head) level, thereafter raised periodically or in steps to a pressure (head) level above the original level, then transferred from such level to a reservoir positioned at a predetermined, relatively lower pressure (head) level, and thereupon drained to an outlet positioned approximately at the level of the original pressure (head) level.

29 Claims, 14 Drawing Figures

METHOD AND APPARATUS FOR CIRCULATING OR PUMPING ORGANO-BIOLOGICAL LIQUIDS, IN PARTICULAR BLOOD

This is a continuation, of application Ser. No. 156,463, filed June 4, 1980 now abandoned.

In effecting the circulation or pumping of blood or similar liquids susceptible to mechanical damage, every conventional method, regardless of the pumping principle in accordance with which such methods operate, results in an at least partial destruction of the red blood cells present in the blood (hemolysis). Surprisingly, hemolysis does not only occur in the actual pumping operation, i.e. in the pump proper, but rather to an extent being significant at least after some time of operation, also in other portions, for example in the feed (inlet) and discharge (outlet) lines or—if provided —the valves. Besides, the conventional blood pumping systems are difficult to sterilize and vent as they rely upon substantially rigid flow cross-sections at least in essential portions thereof. Accordingly, these drawbacks apply even to pump systems wherein the pumping operation is not effected by continuous mechanical squeezing action (roller-type pumps) on the blood, but wherein the blood is pumped or set into flow merely by making use of a difference in level or elevation.

Object of the present invention is the improvement of the methods as outlined above, or of the apparatuses for carrying out such methods, particularly with a view to as gentle or smooth as possible a treatment of organobiological liquids, preferably blood, during pumping or circulation, and at the same time with the object of providing economical and operationally simplified facilities.

Accordingly, the present invention is characterized by maintaining the liquid during the entire passage through the above circulation within a closed loop comprising at least substantially continuous and resilient (elastically flexible) walls.

Hereby, the term "resilient" (elastically flexible) is meant to characterize a consistency of the walls whereby the spaces or cross-sections enclosed by such walls are variable both by external action and under pressure motions within the liquid as such. Depending on the phase of the pumping operation, i.e. the individual method steps, the elastic resilience of the walls should preferably be different, however. While, for instance, the individual connecting lines should be allowed to experience complete collapsing of the interior cross-section only under higher compressive pressure than in the pumping operation proper, the elastic resilience of the containers or reservoirs is substantially higher. These reservoirs should be capable of conforming their volume to the respective volume of blood flowing therethrough already at low pressure variations and without producing any considerable back pressure.

In this way, the inner surface of the walls is capable of automatically adapting itself in any position to the respective local pressure, flow and, if applicable, pulsation conditions of the blood, such that—as the blood is enclosed within such walls throughout the pumping apparatus according to the invention—optimum laminary flow conditions are provided. For the same purposes, all of the cross-sectional (lumen) variations of the tubes show only gradual divergence or convergence. This eliminates shear effects which would be traumatizing or destructive to the blood cells (erythrozytes). In particular, surprisingly it has been found that flow components of the blood directed perpendicularly to the walls cause such destruction of erythrozytes.

The present elastically flexible or resilient structure of the walls allows to impart to the liquid or the blood enclosed within the walls either suction or pressure of limited magnitude or even pulsating pressure variations, as required, from the outside of the walls. It is particularly the possible cooperation of the resilient walls in pulsating blood pressure variations that illustrates the specific advantages of the invention in which the wall system is at the same time formed for optimum physiological compatibility.

As the most preferrable inner lining of the walls treating the blood most carefully, there may be used, e.g. fine polyurethane or silica-free silicone. Furthermore, in accordance with the present method a possible variation is characterized by stimulating, in valve-controlled manner and by controlling the periodic or incremental conveyance (of the liquid), the pressure (head) level above the original liquid pressure (head) level, by applying to the liquid from the exterior of said walls a positive pressure corresponding to the hydrostatic pressure of a given elevation or (pressure head) level.

In the present method, there may even be used valves for controlling the flow cross-sections from the outside of the walls, whereby undesirable backflow in the process may be avoided and additional control or regulation becomes possible, while avoiding contact of the blood with portions of the actively controlled valves.

Finally, the present method in this way also allows the pumping operation to be controlled in fully automatic manner by active valves, while avoiding intolerable hemolysis by the action of the valves.

In an apparatus for carrying out the present method, the reservoirs receiving the liquid or blood, i.e. the venous reservoir or receptacle through which pumping energy is transmitted to the blood, and the container forming the arterial reservoir, are formed as bags of a flexible material, preferably plastics material. These bags are filled and emptied, on the one hand, without any substantial backpressure by simply (freely) receiving and draining the blood. On the other hand, the flexible bag configuration may be utilized, by positioning the bag interiorly of a housing, to apply from the outside a pressure or suction to the liquid enclosed within the bag; owing to the filmlike and elastic bag wall, this can be done in a way being most preserving to the blood, for example in the form of a gas or liquid pressure, whereby increased safety against leakage is provided by using blood substitutes.

The connecting lines and bag-shaped containers are prepared in an integrally connected condition and preferably formed as a single unit. An integrated set of the walls of this type may be marketed in a tightly folded and fully sterilized condition. Besides, pump walls of this kind may be primed with blood substitute during manufacture thereof, such that they need not be vented prior to use thereof. Owing to the resilient material, the free inner cross-sections (lumina) may be of minimum volume, such that the volume of foreign blood serum may be kept at a minimum, whereby the free lumina are only filled up with the blood from the object to be treated upon connection to the latter. Upon termination of the pumping process, the blood contained within the wall system may be substantially fully withdrawn and returned to the object.

This utilization of the volume of the wall system allows to provide relatively wide-lumen flow conditions interiorly of the present pump system without causing excessive blood loss to the object.

The present wall system may be manufactured as a disposable article being fully independent of the other required operating and controlling devices, which article is simply connected to these devices when it is to be used.

In the resilient wall system according to the invention, the valves required for proper pump control may be devised as active valves, namely as valves operating from exteriorly of a wall cross-section or lumen, e.g. of a connecting line. The portions of these valves which act directly on the associated flow cross-section (lumen) are of such configuration as to maintain laminary flow within the walls in every opening and closing phases of the valves; preferably, the valves are anyhow operated only when the flow has come to rest. Thus, these portions are formed with a parabolic or even semi-circular configuration. In addition, the opening and closing process is controlled also in its velocity of motion, such that the shear strain limit of 50 $Nm^{-2}$ being critical with respect to the traumatizing of blood is never exceeded.

In the place of the clamping or pinch-off valves, in preferred embodiment the connecting tubes of the resilient wall system also may be provided with a short tube or hose section having a film-like thin wall (similar to the bag-type containers) only and around which a stationary compartment may be positioned to which a positive pressure may be applied so as to compress the thin tube section and thereby block the passage in the manner of a membrane-type valve. When the pressure (e.g. air pressure) is relieved, the passage is automatically reestablished by the internal pressure within the wall system.

For the automatic control or regulation of these non-jerkily operating valves, both fluids level detector means and a central control unit are provided. In addition, this control unit allows to apply pulsating oscillation to the blood in the various pumping phases or cycles. This pulsating oscillation also may be controlled by the rhythmically coupled oscillation of the circulation of a living object connected to the present pump, in order to support and stimulate the circulation proper or the activity of the heart.

Below, the present invention is described in greater detail in embodiments by referring to the accompanying drawings, wherein:

FIG. 4 is a schematical view, rotated by 90°, of the active valve, showing approximately the operating position according to FIG. 3a;

FIGS. 5a to 5c show a fluid level detector device for the container bags according to e.g. FIGS. 2a to 2c, including sensor arms and light-barrier signal scanning means, in schematical view showing several fluid levels, and in schematical plan view and side elevational view, respectively;

Figure 1A:
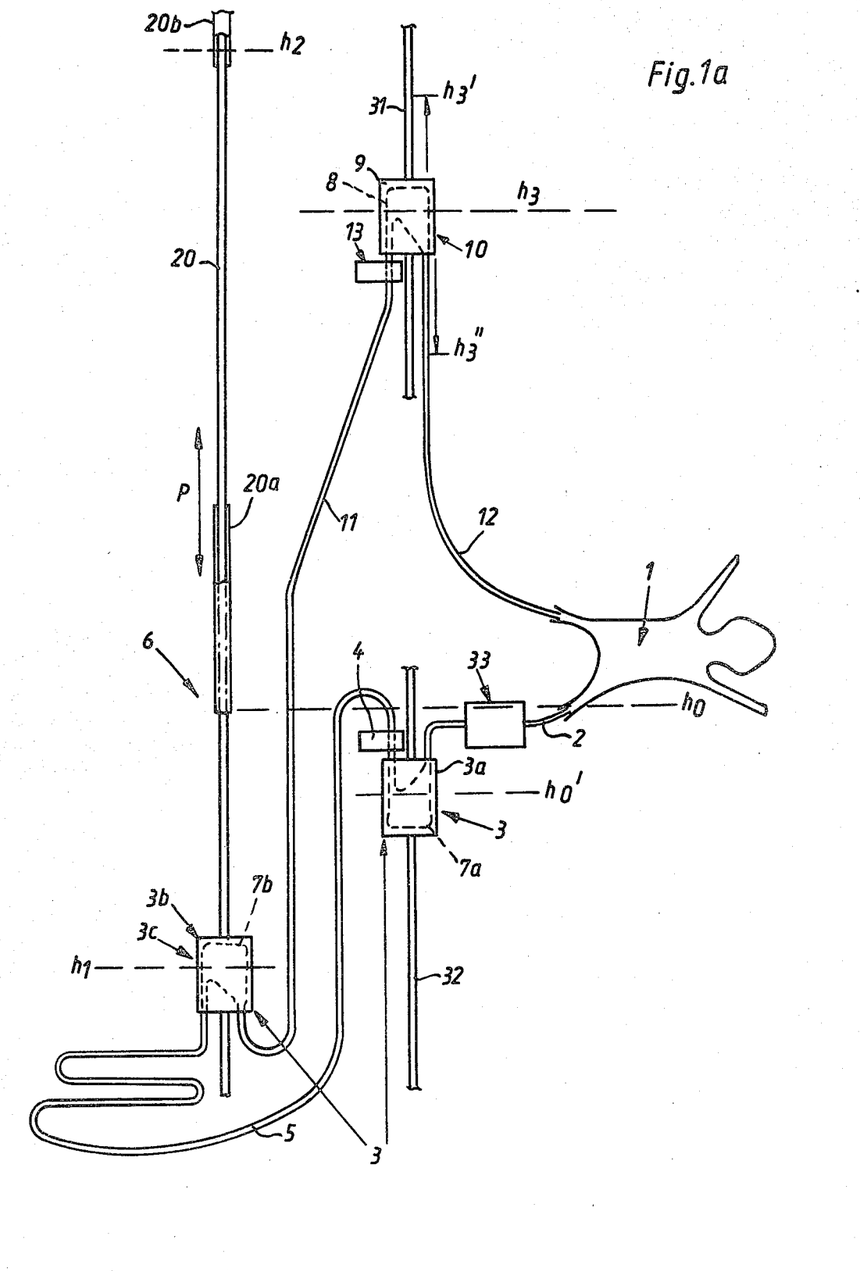
FIGS. 1a and 1b are each a schematical presentation of a basic embodiment of the present pump apparatus in two different working positions.
Figure 1B:
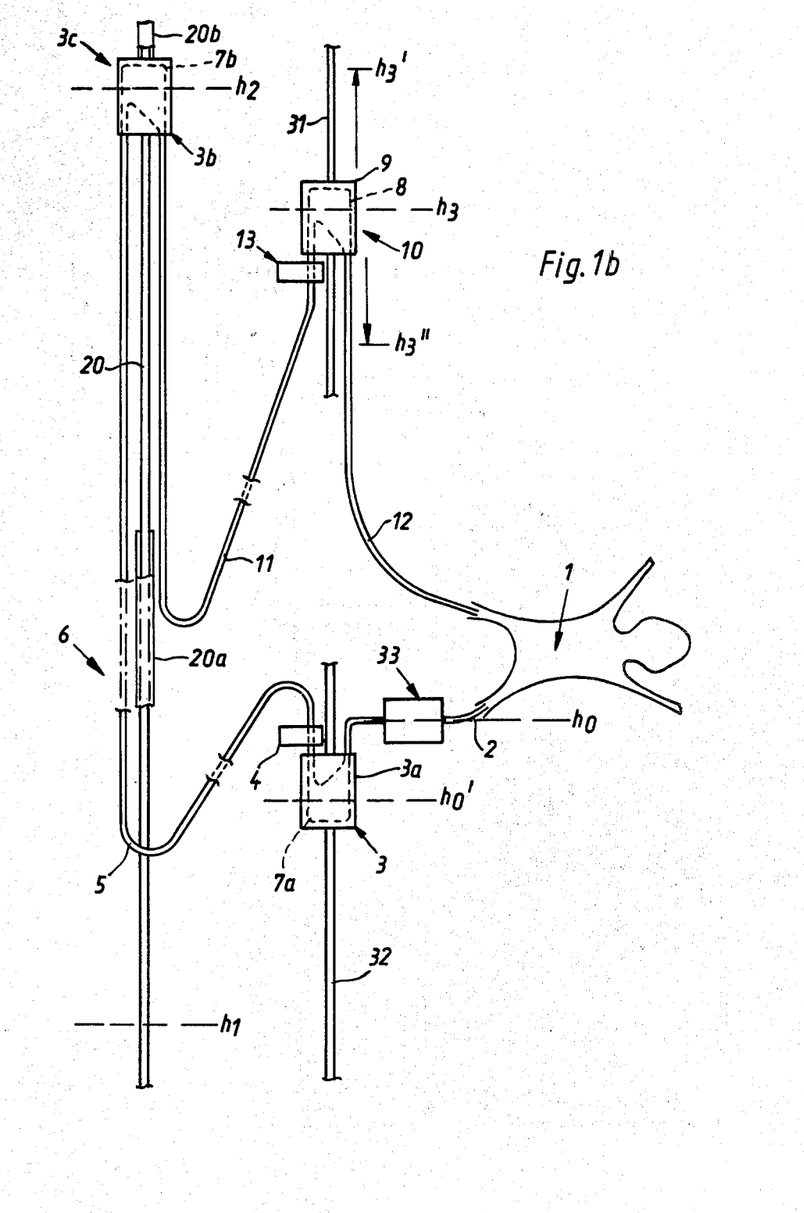

The embodiment illustrated in FIGS. 1a and 1b shows the invention in its fundamental aspects according to which the blood is conveyed in most gentle manner through the complete circulation and pump system in a substantially laminary hydrodynamic flow without the formation of dead zones and zones of stagnating flow.

The frame apparatus for providing the differential pressure which is required for the pumping operation extends, as shown in FIG. 1, from a housing or casing 3a of a venous receptacle (venous reservoir 3), through a connecting line 5 passing from said housing, a subsequent housing 3b for a transporting receptacle 3c and a housing 9, connected by a connecting tube 11 to the transporting receptacle 3c, of a receptacle for continuously returning the circulated blood (arterial reservoir 10) to the arteria of a living organism the blood of which is being circulated. On the venous side, the blood is withdrawn through a drawing tube 2 into the venous reservoir 3, to be returned to the living organism from the arterial reservoir 10 through an arterially connected supply tube 12. This arterial reservoir offers the extra advantage that it may serve for the stabilization of the circulatory pressure even in emergency cases, for instance in a momentary failure of the pump system. For safety reasons, in the vicinity of this arterial reservoir there may be provided also an auxiliary container filled with blood substitute which may be connected into the circuit when the risk arises that the reservoir becomes empty.

The housing 3b for the transporting receptacle 3c is adapted to be raised vertically by means of a device 6 for applying a positive pressure to the liquid to be circulated, for instance on a vertical guide rail 20, from an elevation and thus pressure level ($h_1$) below the living organism connected to the system, to a level ($h_2$) corresponding to the required inlet pressure (e.g. from 150 to 200 mm Hg), said movement taking place incrementally or in steps when vessel 3c has been filled in the elevation of level $h_1$. The guide rail 20 may be telescopingly contractible and/or extensible, for example by a telescoping connection 20a or a telescoping extension 20b, respectively.

Likewise, the housing 3a and 9 of the venous reservoir 3 and of the arterial reservoir 10, respectively, may be adapted to be moved vertically on vertical adjustment or guide rails 31 and 32.

In the pumping process, the blood flows through the venous drawing tube 2 which has connected thereinto blood treatment means 33, such as an artificial kidney (dialyzer) or an oxygenator, to the venous reservoir 3 being positioned in a level $h_0'$ slightly below the position of withdrawal (level $h_0$). As soon as the venous reservoir 3 has been filled by blood, the blood is transferred into the transporting vessel or receptacle 3c which is then moved to a still lower elevation or level $h_1$ relative to level $h_0'$. When the transporting receptacle 3c has been filled, it is raised, as shown in FIG. 1b, to a level $h_2$ sufficiently above the living organism 1, and its contents is transferred in this position to the arterial reservoir 10 positioned slightly lower than level $h_2$ in level $h_3$, whereupon the blood is continuously returned into the arteria of the living organism. The arterial reservoir 10 may be positioned between (vertical) levels $h_3'$ and $h_3''$ as required, such positioning taking place—if necessary—with a predetermined pulsating movement. The venous reservoir may be adjustable in a similar manner. The various vertical positions or elevations h result in corresponding pressure heads.

Connecting tubes 5 and 11 may have connected thereinto an inlet valve 4 and an outlet valve 13, respectively, in order to avoid backflow of blood in the various positions of the transporting receptacle 3c. In the above described pump apparatus, it might do to omit the venous reservoir 3 and/or the arterial reservoir 10; however, continuous and more efficient (boosted) pumping operation may be obtained with the use of these reservoirs.

In the above frame apparatus, the blood is conducted in a closed-loop and substantially continuous system of resilient (elastically flexible) walls, which system comprises, on the one hand, the connecting tubes 5 and 11 as the venous drawing tube 2 and the arterial supply tube 12 which, owing to their elastic resilience, permit their cross-sections to be reduced by externally applied pressure and which also react to pressure surges occuring in the blood with limited resilience, but which neither are kinked during transporting or adjustment movement of the frame apparatus, nor are subject to constriction of their cross-sectional area under the negative pressure action exerted on the blood. In this manner, optimum laminary flow of the blood with a minimum of bloodtraumatizing effect is obtained. In order to avoid surface friction, these tubes or hoses formed of e.g. latex or plastics material are lined with silica-free silicone or fine polyurethane.

Figure 5A:
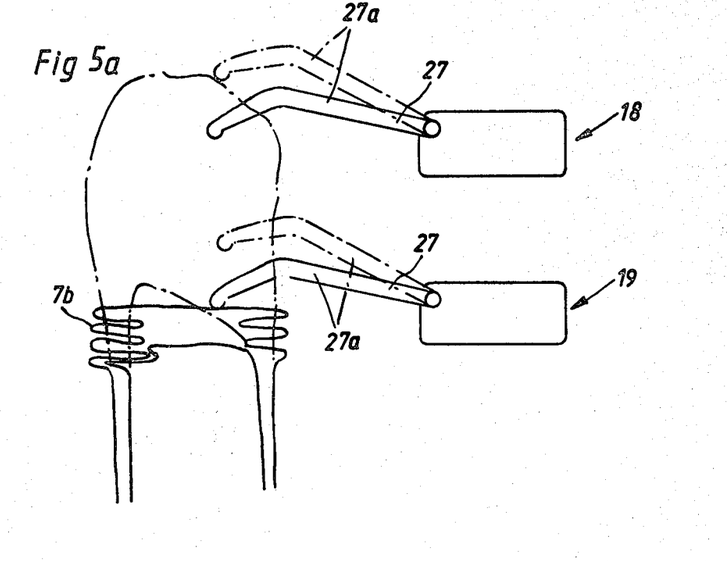
Figure 5B:
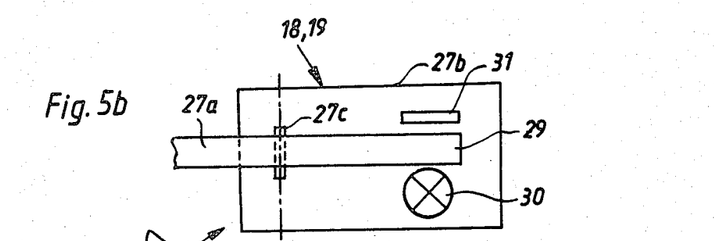
Figure 5C:
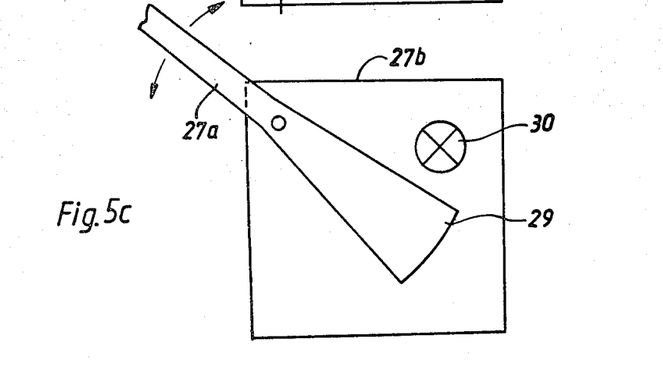

On the other hand, the elastic resilience of the venous and arterial reservoir as well as of the transporting receptacle is provided by plastic bags which, owing to their small wall thickness or flexible walls, provide for laminary flow while at the same time being adapted to expand their volume without any substantial inherent resistance or reduce their volume to substantially zero by collapsing or compression (e.g. FIG. 5a) during the respective filling and emptying processes.

It has been found to be optimal that these plastic bags may show a certain thick-walled configuration so as to provide for laminary flow even if e.g. wrinkles are formed therein. So far, as the material for the lines or tubes and the bags, polyacryl amide or silicate-free or filler-free silicone has been found to offer the maximum blood compatability.

Figures 2A, 2B, 2C:
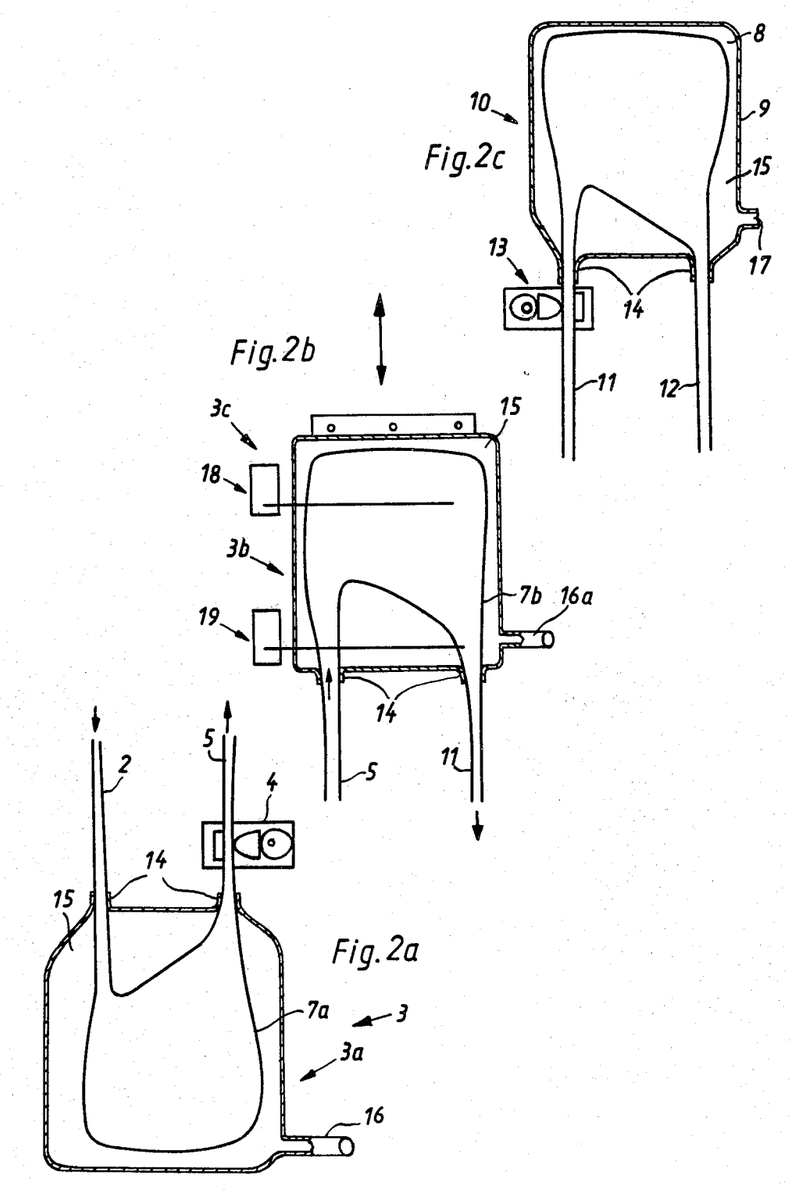
FIGS. 2a, 2b and 2c are enlarged views, in longitudinal section, of the containers used in the pump apparatus according to FIGS. 1a and 1b.

This construction and the arrangement of the plastic bags are shown in FIGS. 2a and 2c. Interiorly of the housing 3a of the venous reservoir 3 (FIG. 2a), the plastic bag 7a is positioned which has its inlet end sealingly connected to the venous drawing tube 2 and its outlet end sealingly connected to the connecting tube 5.

Housing 3a encloses the plastic bag in such a manner that a negative pressure or a positive pressure may be produced in the interior space 15 of the housing through a line connection 16, which pressures act to assist the filling expansion and emptying contraction. On the other hand, the plastic bag acn be readily inserted into housing 3a which may be a split two-piece construction adapted to be opened. In this construction, the tube bushings 14 may comprise a single passage or bushing when tubes 2 and 5 are brought together a short distance in front of housing 3a.

The transporting receptacle 3c (FIG. 2b: plastic bag 7c, interior space connection (15) and the arterial reservoir 10 (FIG. 2c: housing 9, plastic bag 8, interior space connection (17) may be of a similar construction, but connected to the respective other connection, namely connecting tubes 5 and 11, or the connecting tube 11 and the arterial supply tube 12, respectively.

When the apparatus operates solely with pressure head as shown in FIGS. 1a and 1b, the line connections 16, 16a and 17 operate as pressure balance means (vents) to the atmosphere only. However, by having accurately controlled or regulated positive or negative pressures acting through these connections, the pumping operation as such may be effected such that the guide rail may be omitted. In such case, the total interior volume of the tubes or hoses may be reduced, and the apparatus may be constructed so as to occupy less installation space.

Housings 3a, 3b and 9 may have installed thereinto a device for heating the blood. Such heating might be effected also by heating the medium (air or water) filling the interior spaces 15.

Figure 3A:
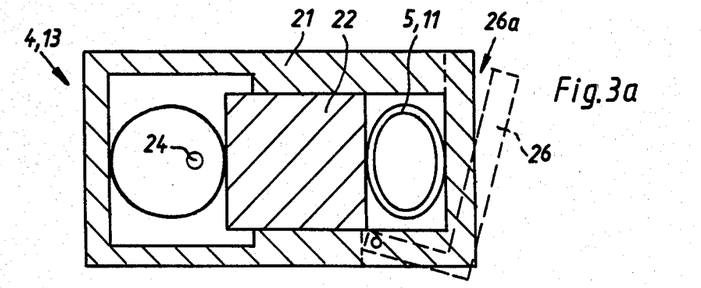
FIGS. 3a and 3b are schematical sectional views of one of the active valves of the present pump system as shown in FIGS. 1a and 1b as well as FIGS. 2a and 2c, in two different working positions.
Figure 3B:
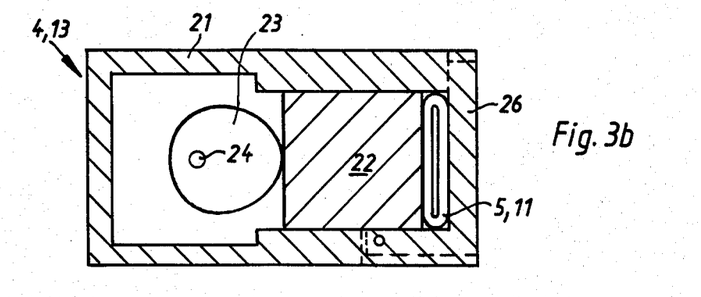
Figure 4:
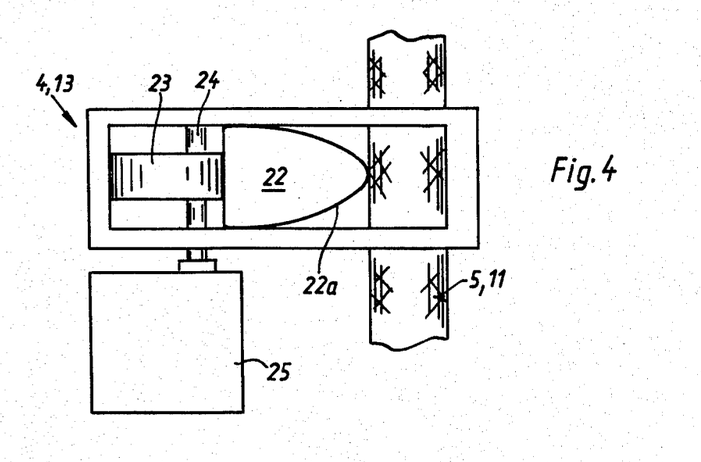

The actively controlled valves, i.e. inlet valve 4 and outlet valve 13 (see FIGS. 2a and 2c) are formed, as shown in FIGS. 3a, 3b and 4, as clamping or pinch-off valves acting on the tube walls from their outer sides. These valves comprise substantially a frame (casing) 21, a servomotor or relay drive 25, an eccentric member 23 mounted on a shaft 24 and the clamping means 22 proper. The connecting tube 5 or 11 to be closed by being pinched off or clamped can be inserted into a closable opening 26a through a portion 26 of the frame 21 being adapted to be swung open. The very clamping surface of the clamping means 22 which acts to pinch off the tube from its outer side, has e.g. an approximately parabolic, semi-circular clamping contour 22a which maintains as laminary as possible a flow interiorly of the tube during variation of its cross-section, even in the course of the opening or closing process. Also, the rate of the clamping or pinch off process is selected to provide optimum preservation of the blood, by selection of the rate of speed of the servomotor and the characteristics of the eccentric member 23. In alternative embodiment, the clamping valve may be operated by other means, for example by hydraulic or pneumatic means.

The measurement of the fluid level existing within the reservoirs and the transporting receptacle, respectively, which is required for automatic operation, may be performed by fluid level detectors (compare e.g. FIGS. 2b and 5a - full condition=18, empty condition=19) through sensors 27 the arms 27a of which sense the degree of filling of plastic bag 7b and—by being mounted on a pivot 27c and a frame 27b—cause the production of a corresponding electrical signal by moving a shutter 29 between a light source 30 and a photosensor 31, which signal may be used for the fully automatic control of the method and apparatus.

Alternatively, the fluid level—particularly when the pumping operation is effected by rhythmically or cyclically filling and emptying the interior spaces 15 with air or water (e.g. with blood substitute)—may be detected by measuring the respectively displaced volume of pressurized medium.

A set of connecting tubes and reservoirs according to the invention, namely comprising the venous drawing tube 2, the connecting tubes 5 and 11, the plastic bags 7a, 7b and 8 as well as the supply tube 12, may be formed either integrally or as a tightly or sealingly connected structure in the form of a disposable mass-production article which, for use, may be placed into the remainder of the frame apparatus in a properly sterilized condition. Such set may be provided for use also in a state as previously filled with blood serum and properly vented (primed), with the inner volume being kept at a minimum by compression of the elements.

Transmission of a slight positive pressure or suction action to the blood volume contained within the wall systems so as to assist the pumping operation, may be effected either by corresponding level (elevation) adjustment or by externally applying pressure on the interior spaces 15 of the housings. The same applies to a pulsating effect which (optionally taking place in the rhythm of the heart and controlled by this rhythm) may support blood circulation.

By the way, the whole process or the apparatus according to the invention, respectively, may be controlled in fully automatic manner, whereby auxiliary measurements of the existing blood pressure taken from the living organism may be used for controlling and regulating the pumping operation, too.

The invention is applicable to any type of extracorporeal blood treatment, such as in a kidney dialyser or an oxygenator; in alternative embodiment, however, the invention is also applicable as a veno-venous pump for the coronary suction of blood in open-heart surgery.

Figure 6:
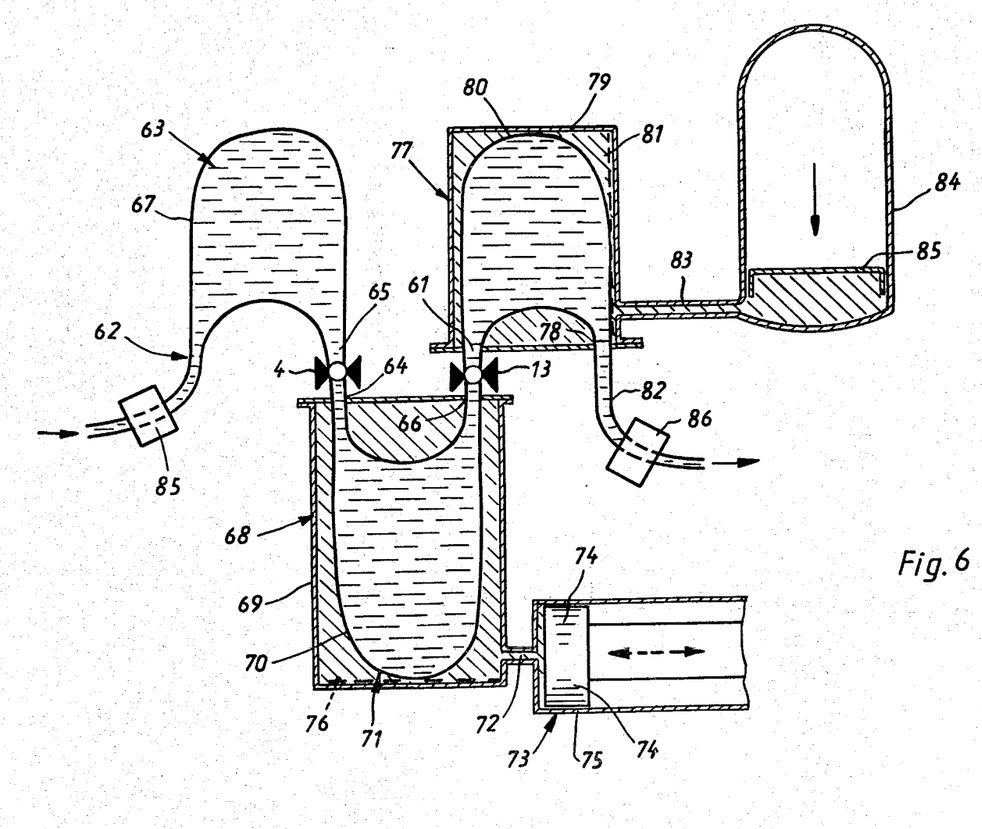
FIG. 6 is a schematical view of an improved embodiment of the invention operating essentially with the controlled use of a pressurized medium.

FIG. 6 illustrates a further embodiment of the invention which, on the one hand is of more compact outer size to save installation space, and which, on the other hand, requires shorter connection passages and, thus, a lower external blood volume. This more compact configuration also facilitates more uniform temperature control of the circulated blood. The embodiment shown in a functional form only in FIG. 6 may be embodied in practice in the form of a closed, thermally insulated housing (not shown) in which the receptacles are positioned side by side with close spacing, wherein the elastically resilient structure comprising connecting lines or conduits and bags, preferably formed integrally, may easily be placed into the housing from one side thereof or from the upper side of the housing into the respectively provided spaces for the bags or in the passages or slots for the connecting lines, respectively. In particular, blood is drained through the venous drawing tube 62 into the venous reservoir 63 comprising an elastically resilient bag 67, and such draining takes place preferably under gravity force only which has the least adverse influence on the systemic circulation.

When a certain blood volume has been collected, the blood is transferred through a connecting line 65 into a transport device 68 comprising a closed, separate housing 69 and an elastically resilient bag 70 as the transport operation reservoir 71 positioned in said housing, and a pump 73 connected through a fitting 72 and composed of a piston or plunger 74 reciprocating within a cylinder 75.

The passages 64 for connecting lines 65 and 66 to the further connecting line 61 of bag 70 are sealed to be fluid tight such that the inner volume of housing 69 surrounding the bag 70 may be filled with a liquid which, by suitable operation of piston 74, may be drawn through fitting 72 into the inner space of cylinder 75 or pumped from said inner space into housing 69, respectively. As the liquid, there may be used a physiological or isotonic normal saline solution which will not be harmful to the blood even if the bag wall is damaged.

The inlet to the bag 70 and the outlet thereof are provided with valves 4 and 13, respectively, of the type shown in FIGS. 3a to 4, which valves are operative to control the closing and opening of connecting lines 61 and 65.

Heating means 76 may be provided to control the blood temperature.

When the venous reservoir 63 (which may be mounted within a not illustrated receptacle open at the upper side) has become full, with valve 4 open and valve 13 closed, the blood, by sucking the liquid into cylinder 75, under the negative pressure thus produced in housing 69 is aspirated into bag 70, whereupon valve 4 is closed so that the venous reservoir 63 may filled up again.

Connecting line 61 opens into the arterial reservoir 77 comprising a similar bag 80 positioned within a housing 79, and passages 78 for lines as well as, optionally, heating means 81. The inner space or volume of this reservoir 77 is likewise filled with a liquid, e.g. physiological normal saline solution, and connected through a pipe connection 83 to a gas spring 84 formed, for example, as (compressed) air chamber and the gaseous content (e.g. air) of which is prevented from direct contact with the liquid by a flexible membrane or diaphragm by being formed as a gas-filled bag.

For transporting the blood from the transport operation reservoir 71 to the arterial reservoir 77, valve 13—with valve 4 being closed—is opened, and the liquid is urged out from the cylinder 75 into the inner space of housing 69. In this way, blood is pumped against the light pressure of gas spring 84 through the connecting line 61 into the bag 80 of the arterial reservoir 77, while displacing the liquid from housing 79 into the air chamber 84. The automatically controlled gas chamber 84 ensures that a sufficient arterial pressure exists under all circumstances.

From the arterial reservoir 77, the supply hose or a supply line 82 then returns to the object to be treated.

The terms "venous" and "arterial" are not intended to exclude such situation in which the pump is connected into the circulation of the object to be treated in a venous-venous or arterial-arterial (or even arterial-venous) configuration. Further, it should be noted that in this embodiment, too, valves 4 and 13 are always closed or actuated not before the blood flow has stopped in the reversing operation.

Owing to the lesser blood filling volume in this embodiment, it is also possible to reduce the volume of physiological plasma substitute solution ("blood substitute") by which the structure comprising the connections and bags is initially filled prior to use and independently of the actuating and control apparatus in an evacuated and sterilized state.

As further shown in FIG. 6, measuring instruments 85 and 86 for the volume measurement of the blood and liquid flow quantities are provided on the inlet and outlet of the pump device, with the measuring or detection signals of these measuring instruments being utilized by a central unit for monitoring and maintaining a uniform flow balance.

Figure 7:
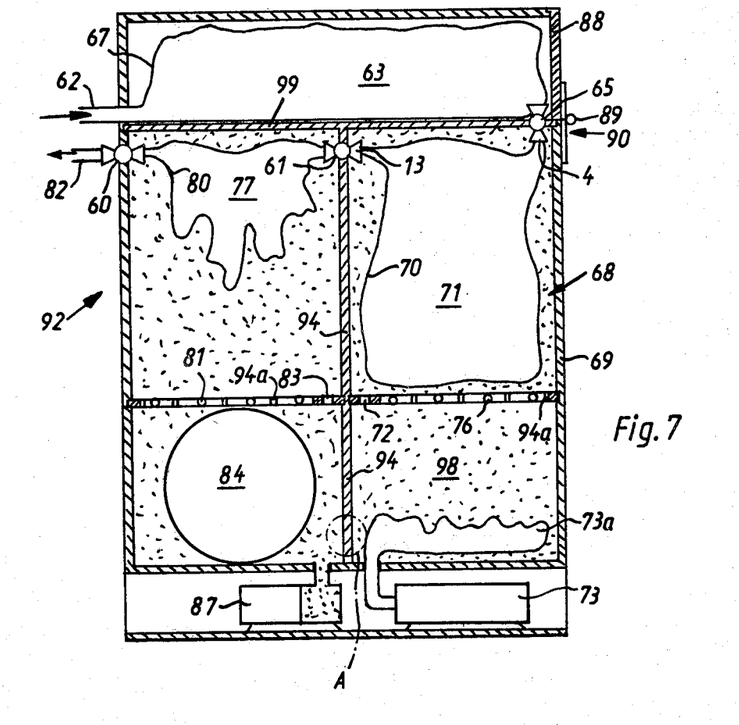
FIG. 7 shows a practical embodiment of the invention, illustrated in longitudinal sectional view and including additional modifications.

In FIG. 7, the blood pump according to the invention is shown as embodied in a three-dimensionally compact construction within a thermally insulating housing 92. This housing 92 encloses all the venous reservoir 63, the transport operation reservoir 71 and the arterial reservoir 77, as well as the gas spring 84 and the pump device 73, wherein the functions of the gas spring 84 through its pipe connection 83 formed as a simple port, and of the pump device 73 including its connection 72 likewise formed as a port, are integrated by separating partitions 94.

In this construction, by a suitable arrangement bags 80 and 70 may be made to float in the liquid within the housing 92, so as to be fully surrounded by the liquid. Alternatively, the bags may rest on the bottom (such as, for instance, bag 67 in FIG. 7) and bulge upwards when filled with blood, with the liquid being above the bag. Also, the bags may be formed as membranes or diaphragms peripherally secured to the partitions 94, which diaphragms may each expand into one of the compartment halves defined thereby, depending on the pressure conditions. In such case, however, sterilization of the separate compartments is difficult.

Figure 8:
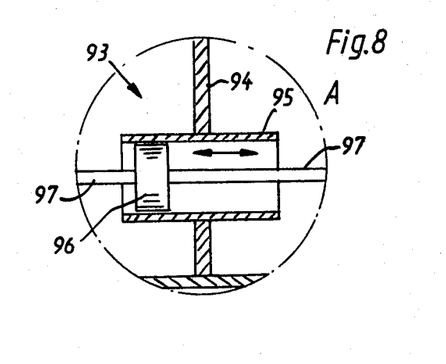
FIG. 8 is an enlarged illustration of a simplified embodiment of a pump circulation device for the liquid surrounding the reservoirs.

The pump device 73 includes an electronically controlled gas (air) pump to inflate a flexible bag 73a within a compartment 98 under electronic control and intermittingly at the pumping frequency, whereby the liquid compresses the bag 70 via the connection 72. FIG. 8 illustrates the state existing approximately at the beginning of such operation cycle. In this state, the bag 80 expands against the pressure of gas spring 84. The partitions 94a may comprise screenlike supports only, and the heating means 81 and 76 may be used to this end.

According to FIG. 8, the liquid surrounding the gas spring 84 may be placed under pulsation by pulsating means 87, whereby the pulsation is transmitted to the blood and, advantageously, also to the systemic circulation, namely, for example, in the rhythm of the heart pulsation to augment the latter.

Instead of the pulsating means 87 (e.g. piston-cylinder unit or membrane) the gas spring 84 per se through a suitable connection may be vibrated in timed fashion. For controlling the pulsation, a further valve 60 (as additionally shown in FIG. 8) may be provided in the supply line 82 (to the object to be treated), which valve has the same construction as valves 4 and 13.

In the embodiment according to FIG. 8, first an intermediate cover 99 supporting the bag 67 may be lifted off the housing 92, whereupon bags 71 and 77 may be installed. Upon filling the housing 92 with liquid, the intermediate cover 99 is attached securely and in fluid tight manner in the sealing plane 90, and bag 67 is arranged interiorly of the cover 88 mounted by means of a hinge 89, such that the bag may freely expand or collapse in the space defined by cover 88.

It is particularly advantageous to replace the gas spring 84 and the pump device 73 in the embodiment according to FIG. 7 by a pump circulation device 93 mounted in the partition 94. As shown in FIG. 8, this device in most straightforward construction may comprise a cylinder 95 including a piston 96 and driven piston rods 97, whereby the liquid is forced either to the side of the transport operation reservoir 71 or to the side of the arterial reservoir 77 with controlled operational timing.

However, in the place of a piston-cylinder pump device, in particularly advantageous manner there may be used also a circulation pump adapted to be reversed in either direction in timed fashion. In this case, a constant-volume pump additionally allows to precisely control the circulated volume.

The additionally desirable pulsation may be superposed to the abovementioned pump circulation device 93. If the pump circulation device 93 is capable of operating with a higher effective frequency, at least the transport operation reservoir (71) may be reduced in size relative to the other reservoirs; however, valve 60 may be included (incorporated) into the pump control system, advantageously by being controlled in response to the pressure.

What we claim is:

1. A method of circulating organo-biological liquids, especially blood, from and back to a living organism wherein liquid received from a living organism into a reservoir is released to a pressure level below its original fluid pressure level, thereafter raised periodically or in steps to a pressure level above the original level, then transferred from such level to a reservoir positioned at a predetermined, relatively lower pressure level, and thereupon drained to an outlet positioned approximately at the level of the original pressure level for return to the organism, characterized by maintaining the liquid during the entire passage through the above circulation from and back to the organism within a closed loop comprising at least substantially continuous and elastically flexible walls substantially devoid of interior means for causing turbulence of the liquid during its passage to provide for optimum laminar flow conditions to avoid shear effects and traumatizing or destruction of blood cells, said walls being made with inner surfaces of a material of optimum physiological compatability with blood and which will minimize destruction of erythozytes, said walls also being made as one integral disposable assembly attachable to rigid parts of supporting structure.

2. The method according to claim 1, characterized in that draining of the liquid takes place under a limited suction applied to the walls from the outside thereof.

3. The method according to claim 1, characterized by applying a positive pressure of limited magnitude to the liquid released to the outlet, from the exterior of said walls.

4. The method according to claim 3, characterized by applying pulsating pressure variations of limited magnitude to the liquid released to the outlet, from the exterior of said walls.

5. The method according to any one of claims 1 to 4, characterized by stimulating, in valve-controlled manner and by controlling the periodic or incremental conveyance of the liquid, the pressure level above the original liquid pressure level, by applying to the liquid from the exterior of said walls a positive pressure corresponding to the hydrostatic pressure of a given elevation or level.

6. The method according to claim 1, characterized in that upon draining of a predetermined volume of liquid, such liquid volume is cut off from further supply by means of controlled valves affecting the flow cross-sections from the exterior of said walls, and by applying to such liquid volume a given positive pressure potential for transferring said liquid volume to said outlet.

7. The method according to claim 6, characterized in that the liquid, upon conveyance thereof to means for returning same, is intermittently separated from the pressure applying means by another valve.

8. The method according to claim 7, characterized in that circulation of the liquid is variably and automatically controlled under the action of central control means, by active operation of said valves and by alternatingly applying positive and negative pressures thereto, while simultaneously automatically measuring the fluid level in the individual circulation stages.

9. Apparatus for circulating organo-biological liquids, especially blood, in a closed system from and back to a living organism comprising:

inlet liquid passage means for receiving the liquid to be circulated from the organism;

a first receptacle connected to said inlet passage means for receiving the liquid by gravity from the organism by being positioned at a lower level relative to the original level of the liquid;

a device connected to said first receptacle for withdrawing liquid therefrom and for applying a limited positive pressure to the withdrawn liquid for conveyance thereof, said device including a second receptacle through which the liquid flows;

a third receptacle connected to said device for receiving liquid therefrom and for uniformly and continuously returning the liquid to the organism;

outlet liquid passage means connected to said third receptacle for returning the circulated liquid to the organism;

liquid passage means serially connecting said first, second and third receptacles; and valve means for controlling the flow through said passage means serially connecting said receptacles, characterized in that:

each of said receptacles is of a collapsible bag-like form;

said receptacles and all said liquid passage means are made of resilient or flexible material as one integral disposable assembly which is attachable to rigid parts of supporting structure;

said valve means are arranged outside said liquid passage means; and said assembly is adapted to be readily prepared for instant operation by being substantially gas-free at least partially pre-filled with a liquid compatible with the liquid to be circulated, e.g., blood.

10. The apparatus according to claim 9, characterized in that the internal volume of the assembly is sterilized and substantially gas-free partially filled with blood substitute.

11. The apparatus according to claim 9, characterized in that said receptacles and all passage means have their inner surfaces each lined with silica-free silicone.

12. The apparatus according to claim 9, characterized in that said receptacles and passage means have their inner surfaces each lined with fine polyurethane.

13. The apparatus according to claim 9 characterized in that in said walls of said passage means connected to said device, at least a section of the respective wall is formed with a membrane-like elastic configuration, said section having disposed thereabout a pressure-tight compartment adapted to be supplied with a controlled pressure for compressing the flow cross-section of the respective passage means in the manner of a membrane-type or diaphragm-type valve.

14. The apparatus according to claim 9 characterized in that the valve means each comprises a clamping valve adapted to open and close the flow cross-section of the corresponding passage means from the exterior of the wall thereof.

15. The apparatus according to claim 9 characterized in that at least one of the receptacles is surrounded by a rigid housing within which a negative or positive pressure may be applied to the receptacle therein and a sensor is provided on said housing for detecting the fluid level in the receptacle therein.

16. The apparatus defined in claim 9 in which the receptacles and all of the liquid passage means are constructed and designed to provide optimum laminary flow conditions to avoid shear effects and traumatizing or destruction of blood cells and wherein the inner wall surfaces of said receptacles and passage means are made of one of fine polyurethane and silica-free silicone for optimum physiological compatability with blood and to minimize destruction of erythozytes.

17. The apparatus according to claim 9, characterized in that said valve means each comprise a frame enclosing the associated passage means and a mechanically operable clamping or pinch off element for compressing or opening the flow cross-section of said passage means.

18. The apparatus according to claim 17, characterized in that said valve means each include means, for actuating said clamping element by a servomotor or by electromagnetic means operating with predetermined motion characteristics.

19. The apparatus according to claim 17, characterized in that the side or surface of said clamping element which compresses and releases the flow cross-section of the respective passage means has a rounded, especially parabolic or semi-circularly curved, configuration which during compression maintains a laminary flow in every phase of operation.

20. The apparatus according to claim 17, characterized in that said frame includes in its side receiving said passage means, a closable opening for inserting said passage means.

21. The apparatus according to claim 9 characterized in that the first receptacle is surrounded by a rigid housing within which a negative pressure may be applied to the first receptacle and that the third receptacle is surrounded by a rigid housing within which a positive pressure may be applied to the third receptacle.

22. The apparatus according to claim 21, characterized in that said housings are adapted to be swung open for inserting said receptacles.

23. The apparatus according to claim 9 characterized in that said device is formed as a transport operation reservoir and comprises a pressure-tight housing enclosing the second receptacle with the inner volume or space surrounding said second receptacle within said housing being filled with a liquid and connected to a pump device by means of which said inner volume may be increased or reduced under timed control.

24. The apparatus according to claim 21 or 23 characterized by means for regulating the temperature of the liquid.

25. The apparatus according to claim 21 or 23 characterized in that the pressure within the housing surrounding said third receptacle is in communication with a pulsating device.

26. The apparatus according to claim 23, characterized in that said pump device includes a gas-receiving displacement membrane or diaphragm adapted to be inflated, in controlled intermitting fashion, up to an automatically controlled maximum pressure exceeding the pressure of said gas spring.

27. The apparatus according to claim 23 characterized in that the third receptacle is enclosed in a pressure-tight housing and wherein the inner volume or space surrounding said third receptacle within said housing is filled with a liquid and is connected to a gas spring which exerts a pressure less than the pumping pressure of said pump device.

28. The apparatus according to claim 27, characterized in that at least said transport operation reservoir, said pump device, said third receptacle and said gas spring are disposed within a common temperature-regulated housing.

29. The apparatus according to claim 28, characterized in that said gas spring and said pump device are combined in a single pump circulation device.

* * * * *